US008138477B2

(12) United States Patent
Gregory

(10) Patent No.: US 8,138,477 B2
(45) Date of Patent: Mar. 20, 2012

(54) THZ INVESTIGATION APPARATUS AND METHOD

(75) Inventor: Ian Stephen Gregory, Cambridge (GB)

(73) Assignee: TeraView Limited, Cambridge (GB)

(*) Notice: Subject to any disclaimer, the term of this patent is extended or adjusted under 35 U.S.C. 154(b) by 0 days.

(21) Appl. No.: 12/301,591

(22) PCT Filed: May 18, 2007

(86) PCT No.: PCT/GB2007/001828

§ 371 (c)(1), (2), (4) Date: Feb. 4, 2009

(87) PCT Pub. No.: WO2007/135382

PCT Pub. Date: Nov. 29, 2007

(65) Prior Publication Data

US 2009/0200472 A1 Aug. 13, 2009

(30) Foreign Application Priority Data

May 19, 2006 (GB) .................................. 0610060.6

(51) Int. Cl.
*G01J 5/02* (2006.01)

(52) U.S. Cl. .................................................... 250/341.1

(58) Field of Classification Search ............. 250/339.07, 250/341.1, 341.7

See application file for complete search history.

(56) References Cited

U.S. PATENT DOCUMENTS 5,513,196 A * 4/1996 Bischel et al. .................. 372/22
6,144,679 A * 11/2000 Herman et al. ................. 372/21
6,348,683 B1 2/2002 Verghese et al.
2004/0065831 A1* 4/2004 Federici et al. ............ 250/341.1
2005/0100866 A1* 5/2005 Arnone et al. ................ 433/215
2005/0156110 A1* 7/2005 Crawely ..................... 250/338.1
2006/0085160 A1* 4/2006 Ouchi ........................... 702/150

OTHER PUBLICATIONS

I. Kawayama et al., "A Tunable Sub-Terahertz Wave Generation and Detection System With a Photomixer and a High-Tc Josephson Junction," *Superconductor Science & Technology*. vol. 19, No. 5, pp. S403-S406. May 1, 2006.

Myadera et al., "Frequency Detecion of Focused Sub-THz Waves Using a High-Tc Josephson Junction," *Physica C*. vol. 426-431, pp. 1726-1730, Oct. 1, 2005.

S. Matsuura et al., "Generation of Coherent Terahertz Radiation by Photomixing in Dipolephotoconductive Antennas", *Applied Physics Letters, AIP*. vol. 70, No. 5, pp. 559-561, Feb. 3, 1997.

(Continued)

*Primary Examiner* — David Porta
*Assistant Examiner* — Marcus Taningco
(74) *Attorney, Agent, or Firm* — Dickstein Shapiro LLP

(57) ABSTRACT

Apparatus for measurement of a sample comprises means for generating electromagnetic radiation comprising a photoconductive device, the generating means is arranged to generate an output signal comprising electromagnetic radiation in dependence upon radiation received by the photoconductive device and to transmit the output signal towards a sample space, the apparatus further comprises a first radiation source and a second radiation source, arranged such that the radiation received by the photoconductive device comprises a mixture of radiation from the first radiation source and radiation from the second radiation source, control means for varying the frequency of the electromagnetic radiation of the output signal by varying the temperature of the first radiation source and/or the temperature of the second radiation source, and detecting means for detecting a response signal.

40 Claims, 7 Drawing Sheets

OTHER PUBLICATIONS

S. Matsuura et al., "Generation of CW THz Radiation by Optical Heterodyne With Diode Lasers and LTG-GaAs Photoconductors." *Microwave Phototonics, 1996. MWP '96. Technical Digest.*1996 International Topical Meeting on Kyoto, New York. pp. 13-16, Dec. 3, 1996.

L. Spencer et al., "Homodyne Detection Up to 2 THz Using Continuous Wave Laser Diodes." *Infrared and Millimeter Waves and 13th International Conference on Terahertz Electronics*, 2005, pp. 249-250, Sep. 19, 2005.

I.S. Gregory et al., "Multichannel Continuous-Wave Terahertz Imaging," *Infrared and Millimeter Waves and 13th International Conference on Terahertz Electronics*, 2005. pp. 46-47, Sep. 19, 2005.

* cited by examiner

Curve fitting examples

THZ INVESTIGATION APPARATUS AND METHOD

The present invention relates to a terahertz investigation system and apparatus, and in particular to an apparatus and method which may be used to gather structural and compositional information from a substance, using spectroscopy at frequencies in the terahertz range, for instance in the range 0.1-10 THz.

The terahertz (THz) region of the electromagnetic spectrum lies between the microwave and infra-red frequencies, and may be harnessed for a wide variety of imaging and spectroscopy applications. Many such applications depend upon the unique properties of THz radiation, combining features from both infrared and microwave technologies, thus permitting imaging through many materials that are opaque at optical frequencies. In addition, many substances exhibit characteristic terahertz spectra, and consequently may be characterised, or even detected and identified using this signature. Imaging and spectroscopy can be performed simultaneously, to yield spectral information at each image pixel—and behind barriers—a property unique to terahertz technology. A number of applications have been identified in industrial inspection, medical imaging and the pharmaceutical and semiconductor industries.

Most substances exhibit spectral features in the near and mid-infrared owing to rotation and vibration of individual bonds between the atoms in the molecules. In contrast, the vibrations of the weaker hydrogen bonds and van der Waals forces in a crystal lattice occur at terahertz frequencies, giving rise to terahertz spectra. These features do not occur at the lower frequencies used in millimetre-wave imaging.

One form of a semiconductor terahertz source which is known is a photoconductive switch triggered by short (femtosecond) pulses of light from a near-infrared laser. The laser is focussed to the point of a voltage-biased, highly resistive semiconductor device. In the absence of illumination, there is no current flow. When the pulse arrives, the stored energy discharges, creating charge carriers. The acceleration of charge carriers, flowing within electrodes designed as antennas, radiates pulses of terahertz frequency radiation.

An alternative known terahertz source is a system based on photo(conductive) mixing. Terahertz emission and detection is possible using a terahertz beat frequency between two continuous-wave (cw) lasers instead of the pulsed laser. Despite producing monochromatic terahertz waves, spectroscopy can be achieved either by tuning the output frequency across a range, or by working simultaneously with multiple discrete frequencies.

The mechanism behind the generation of terahertz radiation in a cw device is very similar to that in pulsed terahertz technology. A near-infrared beam, containing the beat frequency between two continuous-wave (cw) lasers, is used to modulate the conductance of a biased photoconductive switch at the terahertz difference frequency. Electrical terahertz oscillations are produced, which are transmitted into free space via an antenna and lens.

Like the optical stimulus, the terahertz radiation is emitted as a continuous-wave with a very narrow instantaneous bandwidth, typically much less than 1 GHz. However, the spectroscopic function can be retained by scanning the output across the frequency range of interest, by tuning the frequency of one (or both) of the lasers.

A pulsed (broadband) terahertz spectrometer gathers the spectral data for all frequencies present in the pulse simultaneously. The plotted spectrum must be obtained using the Fourier transform of the sampled time-domain waveform. In this case, both the spectral range and resolution are limited exclusively by the constraints of the time-delay sweep used to sample the electric field profile of the terahertz pulse. For a reasonable acquisition time to be retained, the range of the sweep must be limited to a few tens of picoseconds, leading to relatively poor values for the spectral resolution, of order 10 GHz. While sufficient for the detection of broad features in solids, this cannot be utilised for the measurement of narrow absorption lines in gases.

In contrast, a continuous-wave terahertz spectrometer based on photomixing can gather the spectral data directly in the frequency domain, alleviating the requirement of a Fourier transform. This is achieved by sweeping one or both of the optical lasers through an appropriate frequency range, collecting the data points for the spectrum in a sequential fashion.

Various systems based on the continuous-wave terahertz photomixing concept have been suggested, using different types of laser source and different methods to tune the optical frequency so as to produce a variable terahertz difference frequency in the appropriate range.

In one suggested system, two single-mode visible dye lasers are mixed in a photoconductor. A silicon composite bolometer, cooled to 4.2 K using liquid helium, is used for detection.

In another suggested system, two external grating-stabilised diode lasers are used to pump a photomixer, again with a bolometer for detection. Rough tuning is by use of a precision screw to move a grating, whereas fine tuning is via piezo control of the grating. The latter, used for the frequency sweep, offers a mode-hop free tuning range of only 10 GHz, although the measured linewidth was approximately 5 MHz.

In a variation on the above suggested system, one amplified diode laser is used together with a Ti:Sapphire ring laser pumped by an argon ion laser. Tuning is achieved by an intracavity Lyot filter in the Ti:Sapphire laser, mechanically driven via a computer-interfaced stepper motor. Like femtosecond lasers, pumped Ti:Sapphire cavities are relatively costly and bulky, and this places restrictions on the total size and cost of the terahertz system, limiting its suitability for some applications.

In one further suggested system, cw terahertz radiation is generated in a vertically integrated structure by mixing two Ti:Sapphire laser beams. Tuning of the Ti:Sapphire lasers in this case is achieved using a commercial edge-servo control on a Fabry-Perot etalon cavity. Again a bolometer is used for detection.

All of the systems mentioned above use a bolometer for detection, which presents particular disadvantages as, typically, bolometers are bulky and expensive and require the use of liquid helium. Furthermore, a bolometer does not allow for phase sensitive detection.

An apparatus which includes a photoconductive switch as a terahertz source but which does not use a bolometer for detection has been suggested in Applied Physics Letters, 87, 134105 (2005). The apparatus is designed to investigate the response characteristics, and the noise characteristics, of a photomixing transmitter and receiver (transceiver). The sensitivity of the photomixing detector is modulated using two laser sources. The same two laser sources are used to modulate the conductance of a biased photoconductive switch in the transmitter. The two laser sources described are a temperature-tunable distributed feedback laser and an external cavity diode laser in a Littman external grating configuration. The frequency of the terahertz radiation is swept between 100 and 700 GHz by tuning of the external cavity diode laser. Within that range, mode-hop free tuning of 16 GHz is obtained.

All of the systems and apparatus mentioned above, including the apparatus described in the preceding paragraph, depend upon a mechanical element for tuning the frequency, typically a piezoelectric element which controls the laser cavity. The use of a mechanical element for tuning the frequency presents disadvantages, for instance being bulky, with associated mechanical control and driving circuitry introducing noise into the system and requiring careful design and shielding. Furthermore, only limited mode-hop free tuning is provided, typically 16 GHz or less. Also, noise introduced by the use of a mechanical tuning element usually rises rapidly with scanning speed, thus limiting scan rates in practice. Finally, the use of a mechanical element also leads to a physical movement of beam direction, which in addition to introducing noise makes it difficult to maintain a stable coupling of the laser beam, for instance into an optical fibre.

Furthermore, each of the lasers chosen for use in known cw terahertz spectrometers presents particular disadvantages. For instance, pumped Ti:Sapphire cavities are relatively costly and bulky, as are femtosecond lasers, and this places restrictions on the total size and cost of terahertz systems using such lasers, limiting their suitability for some applications.

Other lasers have limited, mode hop-free tuning ranges making them useful for spectroscopy only over a limited frequency range. For instance, while standard external cavity or DBR single mode diode lasers may be nominally tuned using either the electrical current or the cavity temperature, neither is ideal for a widely tunable and versatile spectroscopy system. Electrical tuning produces a continuous tuning range of a few tens of GHz at most, which is insufficient for all but the most specialised gas phase applications. Temperature tuning, on the other hand, can produce a wide tuning range of several THz, but this involves many mode hops rather than a continuous sweep, and so is not suited to spectroscopic applications.

It is an aim of the present invention to provide an improved, or at least alternative, terahertz apparatus and method.

Accordingly in a first aspect of the invention there is provided apparatus for measurement of a sample, comprising:— means for generating electromagnetic radiation comprising a photoconductive device, the generating means being arranged to generate an output signal comprising electromagnetic radiation in dependence upon radiation received by the photoconductive device and to transmit the output signal towards a sample space; a first radiation source and a second radiation source, arranged such that the radiation received by the photoconductive device comprises a mixture of radiation from the first radiation source and radiation from the second radiation source; control means for varying the frequency of the electromagnetic radiation of the output signal by varying the temperature of the first radiation source and/or the temperature of the second radiation source; and detecting means for detecting a response signal.

Thus, the use of a mechanical element for varying the frequency of electromagnetic radiation, for instance by moving a grating or etalon, may be avoided and a compact apparatus able to tune to desired frequencies rapidly may be provided.

The apparatus may be an apparatus for carrying out spectroscopic measurements on a sample. The apparatus may be particularly suitable for carrying out gas phase spectroscopic measurements.

Alternatively or additionally the apparatus may be an apparatus for determining whether a particular substance of interest is present or absent. Such a substance of interest may be the sample or may form part of the sample, and may, for instance be concealed within the sample. The substance of interest may, for instance, be concealed on the body of a person, for instance within clothing, or within luggage or within a parcel or envelope. The substance of interest may be concealed behind a barrier.

Preferably the control means is adapted to vary the frequency of the electromagnetic radiation of the output signal by varying both the temperature of the first radiation source and the temperature of the second radiation source The sample space is a space or region where a sample may be present. The sample space may be located within the apparatus or external to the apparatus. The response signal comprises electromagnetic radiation arriving at the detector from the sample space.

When a sample is present in the sample space then the electromagnetic radiation of the output signal from the generating means may interact with the sample in one or more of a variety of different ways, dependent on the physical and electronic structure of the sample, and dependent on the frequency and phase of the electromagnetic radiation. The electromagnetic radiation may, for instance, be absorbed, reflected, re-emitted and/or shifted in phase or frequency. Electromagnetic radiation received at the detector from the sample can be considered to be a response signal from the sample in response to the electromagnetic radiation applied to the sample.

The detecting means may be arranged to receive electromagnetic radiation from substantially the same direction as a direction towards which the generating means is adapted to transmit electromagnetic radiation. For instance, the detecting means may be arranged to be on the opposite side of the sample space to the generating means.

In that case, if a sample is present in the sample space, the response signal may comprise electromagnetic radiation from the generating means which has been transmitted through the sample. The form of the response signal may, in that case in particular, be dependent on absorption of electromagnetic radiation on its passage through the sample.

Alternatively, the detecting means may be arranged to receive electromagnetic radiation from substantially the opposite direction to a direction towards which the generating means is adapted to transmit electromagnetic radiation. For instance, the detecting means may be arranged to be on the same side of the sample space as the generating means.

In that case, if a sample is present in the sample space, the response signal may comprise electromagnetic radiation from the generating means which has been reflected from the sample.

The photoconductive device may comprise a photoconductive switch. Preferably the photoconductive devices comprises a semiconductor material whose electrical conductivity varies in dependence upon the amplitude of radiation of appropriate frequency applied to the semiconductor material.

Preferably the electromagnetic radiation of the output signal comprises continuous wave (CW) radiation. By having an output signal comprising continuous wave (CW) radiation, it may be ensured that a sample is subject to only a narrow band of frequencies, or a single frequency, at any one time, thus enabling frequency selective measurement of the sample. Preferably the output signal comprises electromagnetic radiation that has a single value of frequency, or a narrow band of frequencies, for a specified period of time.

Preferably the radiation from the first radiation source comprises continuous wave (CW) radiation and the radiation from the second radiation source comprises continuous wave (CW) radiation.

Thus a particularly effective way of providing an output signal comprising continuous wave (CW) radiation may be obtained. Also, the characteristics of the radiation from the first radiation source and the radiation from the second radiation source may be more easily and accurately controlled if the radiation is continuous wave (CW) radiation.

Preferably the output signal comprises electromagnetic radiation having a frequency/power spectrum with a half-power width of less than 10 GHz, preferably less than 1 GHz, and more preferably less than 100 MHz. The electromagnetic radiation may even have a frequency/power spectrum with a half-power width of less than 100 MHz, for instance between 10 MHz and 100 MHz.

Thus, the response of a sample to a well-controlled and narrow band of frequencies may be investigated. A series of measurements may be carried out, with each successive measurement in the series investigating the response of the sample to a different narrow band of frequencies.

Typically, as used herein reference to the frequency of the electromagnetic radiation of the output signal is a reference to the centre frequency of a, usually narrow, band of frequencies. For the purposes of many measurements, for instance spectroscopic measurements, the band of frequencies may be narrow enough for the electromagnetic radiation to be considered as having a single value of frequency.

Preferably the generating means comprises an antenna arranged so that the value of the electrical current through the antenna is dependent on the conductivity of the photoconductive device, and preferably the conductivity of the photoconductive device is dependent on the mixture of radiation received by the photoconductive device.

The theoretical frequency resolution may thus be limited only by the linewidth of the optical laser beams (and not by the properties of a Fourier transform which may typically be used to analyse detection signals in the case where pulsed radiation is applied to a sample) enabling detection of narrow spectral features, as in gas phase spectroscopy. In addition, the ability to sample only a desired small subset of a spectrum may be provided, thus providing a significant speed advantage.

Preferably the apparatus is arranged so that the frequency of the electromagnetic radiation of the output signal is dependent on the difference between the frequency of the radiation from the first radiation source and the frequency of the radiation from the second radiation source.

Thus, accurate control of the frequency of the electromagnetic radiation of the output signal may be provided.

Preferably the apparatus is arranged so that the frequency of the electromagnetic radiation of the output signal is dependent on a beat frequency of the mixture of radiation from the first radiation source and radiation from the second radiation source received at the photoconductive device The control means may be adapted to vary the frequency of the electromagnetic radiation of the output signal within a selected range of frequencies.

Preferably the control means is adapted to vary the frequency of the electromagnetic radiation of the output signal so as to provide electromagnetic radiation successively at each of a plurality of frequencies in the selected range of frequencies.

By way of example, the output signal may comprise continuous wave electromagnetic radiation having a narrow band of frequencies centered around a particular centre frequency, and the output signal may then change, to comprise continuous wave electromagnetic radiation having a narrow band of frequencies centered around another centre frequency. Those centre frequencies may be the plurality of frequencies.

Preferably the control means is adapted to vary the frequency of the electromagnetic radiation of the output signal so as to scan the frequency of the electromagnetic radiation of the output signal across the selected range of frequencies or part of the selected range of frequencies.

The selected range of frequencies may have a magnitude ≦10 THz, or ≦5 THz, or ≦2.5 THz.

The selected range of frequencies may be in the range from 0 THz to 10 THz, preferably in the range from 0 to 5 THz, more preferably in the range from 0 THz to 2.2 THz.

The selected range of frequencies may be 0 THz to 10 THz, or 0 to 5 THz, or 0 THz to 2.2 THz, or 0 THz to 2.5 THz, or 0.5 THz to 3.0 THz. Alternatively, the selected range of frequencies may be a sub-range falling within one or more of those ranges.

Preferably the control means is adapted to vary the temperature of the first radiation source and/or the second radiation source in such a way as to ensure that no mode-hop occurs in the first radiation source or the second radiation source.

Preferably the control means is adapted to vary the frequency of the electromagnetic radiation within the selected range of frequencies without mode hop occurring in either the first radiation source or the second radiation source.

Preferably, the control means is adapted to vary the temperature of the first radiation source and/or the second radiation source in such a way as to ensure that no mode-hop occurs in the first radiation source or the second radiation source for a magnitude of range of frequency of the electromagnetic radiation of the output signal ≧2 THz, preferably ≧2.3 THz, more preferably ≧2.5 THz.

For instance the lasers may be set up to provide a tuning range of 1150 GHz, giving a range of frequency of electromagnetic radiation of 2.3 THz. Such a tuning range may be provided, for certain lasers, by varying the temperature of the laser between 5° C. and 45° C. A greater tuning range for those lasers may be provided by increasing the temperature range over which the temperature varies. Increasing the temperature may ultimately decrease laser lifetime, so preferably the temperature range is selected in dependence upon desired frequency range and in dependence upon likely laser lifetime.

The avoidance of mode-hop can be important, particularly in spectroscopy measurements. Mode-hop may introduce excess noise into a measurement, and also may make it difficult or impossible to carry out measurements at a succession of increasing or decreasing frequencies. Indeed, the occurrence of mode-hop may make it impossible to take measurements at certain frequencies at all.

The control means may be adapted to vary the temperature of the first radiation source within a first pre-determined range of temperature and to vary the temperature of the second radiation source within a second pre-determined range of temperature.

Each of the first pre-determined range of temperature and the second pre-determined range of temperature may be a range of temperature within which no mode hop occurs in the first radiation source or in the second radiation source respectively.

The width of each of the first pre-determined range of temperature and the second pre-determined range of temperature may be ≦20K, preferably ≦40K, more preferably ≦50K.

Preferably the frequency of the radiation emitted by the first radiation source at the lowest extreme of the first pre-determined range of temperature is different from the frequency of the radiation emitted by the second radiation source at the lowest extreme of the second pre-determined range of temperature.

The frequency of the radiation emitted by the first radiation source at the highest extreme of the first pre-determined range of temperature may be substantially the same as the frequency of the radiation emitted by the second radiation source at the lowest extreme of the second pre-determined range of temperature.

Thus, the frequency of the electromagnetic radiation of the output signal can be selected to be any value in a wide range of frequencies.

Preferably the control means is adapted to maintain the frequency of the radiation from the first radiation source substantially constant and the frequency from the second radiation source substantially constant for a pre-determined period of time, and preferably the pre-determined period of time is at least 50 ms.

The detecting means may comprise a further photoconductive device.

The use of a photoconductive device in the detecting means is advantageous since it may remove the liquid helium, bulk, and cost associated with a bolometer, whilst also enabling phase sensitive detection if so desired. The latter allows the apparatus to measure additional information, such as that associated with (or derived from) the refractive index of the sample.

The detecting means may have a sensitivity of detection of the response signal which is modulated at a modulation frequency in dependence upon modulating radiation received by the photoconductive device.

Preferably the detecting means is arranged so that the modulating radiation received by the photoconductive device comprises a mixture of radiation from at least two radiation sources, and the control means is adapted to vary the modulation frequency at which the sensitivity of detection is modulated by varying the temperature of at least one of the at least two radiation sources.

The feature mentioned in the preceding paragraph is particularly important and so in a further independent aspect of the invention there is provided apparatus for measurement of a sample, comprising:—means for generating electromagnetic radiation, arranged to generate an output signal comprising electromagnetic radiation and to transmit the output signal towards a sample space; detecting means for detecting a response signal, the detecting means comprising a photoconductive device and being arranged so that the sensitivity of detection of the response signal is modulated at a modulation frequency in dependence upon modulating radiation received by the photoconductive device; a first radiation source for the detecting means and a second radiation source for the detecting means, arranged such that the modulating radiation received by the photoconductive device comprises a mixture of radiation from the first radiation source for the detecting means and radiation from the second radiation source for the detecting means; and control means for varying the modulation frequency at which the sensitivity of detection is modulated, the control means being adapted to vary the modulation frequency by varying the temperature of the first radiation source for the detecting means and/or the temperature of the second radiation source for the detecting means.

Thus, each response signal may preserve both amplitude and phase information and that information may be obtained by suitable processing of the response signal.

Preferably the detecting means comprises an antenna arranged so that value of electrical current through the antenna is dependent on the conductivity of the photoconductive device, and preferably the conductivity of the photoconductive device is dependent on the mixture of radiation received by the photoconductive device.

Preferably the first radiation source for the detecting means is the first radiation source and the second radiation source for the detecting means is the second radiation source.

Thus, the relationship between the output signal, the response signal and a detection signal may be known accurately. The detection signal may be considered to be a homodyne signal as the sensitivity of detection is modulated with the same frequency as the output signal.

The apparatus may further comprise guide means for guiding radiation from the first radiation source and the second radiation source to the photoconductive device of the generating means and to the photoconductive device of the detecting means.

The guide means may comprise delay means adapted to provide a delay between radiation from the first radiation source and the second radiation source being received at the photoconductive device of the generating means and being received at the photoconductive device of the detecting means.

Preferably the control means is adapted to control the length of the delay to be a desired delay time. Thus, the response signal at a particular phase or phases may be investigated.

The control means may be adapted to vary the delay time.

Preferably the delay means is adapted to vary the delay time with a pre-determined frequency, and preferably the delay means is adapted to dither the delay time at a pre-determined frequency.

Thus, the response signal may comprise the response of a sample across all phases. To extract the amplitude of the response signal, the response signal as a function of time may be fitted to a function representing the variation of the delay time. So, for instance, the response signal as a function of time may be fitted to a sinusoid representing the dithering of the delay time.

The detecting means may be adapted to generate a detection signal representative of the response signal, and the apparatus further comprises processing means for processing the detection signal.

In the simplest case the detection signal may, for instance, be a voltage or current induced in an antenna due to receipt of the response signal. Alternatively the detection signal may be derived from a voltage or current induced in the antenna, for instance by amplifying and/or smoothing and/or selecting part of and/or otherwise processing the voltage or current induced in the antenna.

The processing means, for instance a control computer, may be adapted to carry out a variety of signal processing techniques on a detection signal or signals, if desired. Such signal processing techniques may include signal averaging, signal summing, data fitting, data smoothing, selection of portions of data, and statistical analysis. A process which may be carried out by the processing means on a detection signal may usually, alternatively, be carried out on an a sum or average of a plurality of detection signals.

In one example of a measurement using the apparatus the output signal may comprise first continuous wave electromagnetic radiation having a narrow band of frequencies centered around a particular first centre frequency, and the output signal may then change, to comprise second continuous wave electromagnetic radiation having a narrow band of frequencies centered around a different, second centre frequency. In that case, the response signal received at the detecting means during the time whilst the first continuous wave electromagnetic radiation was applied may be considered to be a first response signal, and the response signal received at the detecting means during the time whilst the second continuous wave electromagnetic radiation was applied may be considered to be a second response signal.

Preferably the processing means is adapted to fit the variation of the detection signal with time to a function.

The processing means may be adapted to compare the detection signal to a reference.

The reference may be obtained from a calibration measurement, and in particular may be obtained from a calibration measurement performed using the apparatus when no sample is present. The processing means may be adapted to compare the amplitude of each detection signal to a respective reference amplitude, preferably obtained from a calibration measurement. The processing means may be adapted to subtract from the amplitude of each detection signal a respective reference amplitude, or to divide the amplitude of each detection signal by a respective reference amplitude. The processing means may be adapted to perform a deconvolution calculation, for instance using the amplitude of each detection signal and a respective reference amplitude. The processing means may be adapted to divide each detection signal by a reference signal representing incident power, to obtain transmitted power as a function of incident power.

Preferably the processing means is adapted to compare the detection signal to a pre-determined threshold, and preferably the processing means is adapted to generate an alarm signal in dependence on the comparison. The processing means may, in particular, be adapted to compare the amplitude of a detection signal to a pre-determined threshold, or to compare the amplitude of each detection signal of a plurality of detection signals to a respective pre-determined threshold, and preferably the processing means is adapted to generate an alarm signal in dependence on the comparison.

At least one of, and preferably each of, the first radiation source, the second radiation source, the first radiation source for the detecting means and the second radiation source for the detecting means comprises a respective temperature-tunable laser, preferably a diode laser.

Preferably at least one, and preferably each, of the temperature-tunable lasers comprises a respective distributed feedback (DFB) laser. Such sources may be especially well suited for use with fibre optic technology, and optical amplifiers are readily available.

Preferably the or each DFB laser may be temperature-tuned over a spectral range of over 1100 GHz without mode-hop. Typically, in a DFB diode, the Bragg grating (the frequency selector) is integrated into the active section of the semiconductor device. Preferably single-frequency operation narrow linewidths are obtained without any external optics.

The or each temperature-tunable laser may be adapted to output near infra-red radiation or infra-red radiation.

The or each temperature-tunable laser may be adapted to output radiation with a centre wavelength in the range 760 nm to 1090 nm, preferably 770 nm to 870 nm.

Preferably the or each temperature-tunable laser, in operation, is tuned so that the wavelength varies by an amount between 1.5 nm and 2.7 nm, preferably by an amount between 2 nm and 2.5 nm.

Preferably the apparatus further comprises a sample cell adapted to be located in the sample space and to contain a sample, and preferably the sample cell is adapted to contain a gaseous sample.

The means for generating electromagnetic radiation may arranged to generate electromagnetic radiation having a coherence length $\geqq$5 m, preferably $\geqq$10 m, and more preferably $\geqq$15 m. The coherence length may even be $\geqq$20 m. The coherence length may be between 5 m and 20 m, preferably between 10 m and 15 m, preferably about 15 m.

Thus, the apparatus may be used to measure a sample, or substance of interest, which is or may be present at a large distance from the means for generating electromagnetic radiation, or which is or may be present anywhere within a large range of distance from the means for generating electromagnetic radiation. That feature is particularly useful if the apparatus is used to detect the presence or absence of a sample or substance of interest which may or may not be present concealed about a person or within a larger item as in such a situation the position, or possible position, of the sample or substance of interest may not be known.

The apparatus may be a terahertz spectrometer.

In a further independent aspect of the invention there is provided a method of measurement of a sample, comprising:—generating an output signal comprising electromagnetic radiation by applying a mixture of radiation from a first radiation source and radiation from a second radiation source to a photoconductive device, and transmitting the output signal towards a sample space; varying the frequency of the electromagnetic radiation of the output signal by varying the temperature of the first radiation source and/or the temperature of the second radiation source; and detecting a response signal.

In another independent aspect of the invention there is provided a method of measurement of a sample, comprising:—providing means for generating an output signal comprising electromagnetic radiation and transmitting the output signal towards a sample space; providing a detecting means for detecting a response signal; modulating the sensitivity of detection of the detecting means at a modulating frequency by applying a mixture of radiation from a first radiation source and from a second radiation source to a photoconductive device included in the detecting means; and varying the frequency at which the sensitivity of detection is modulated by varying the temperature of the first radiation source and/or the temperature of the second radiation source.

Any feature in one aspect of the invention may be applied to another aspect of the invention, in any appropriate combination. In particular, apparatus features may be applied to method features and vice versa.

Preferred features of embodiments of the invention will now be described, purely by way of example, and with reference to the accompanying drawings in which:—

Figure 1:
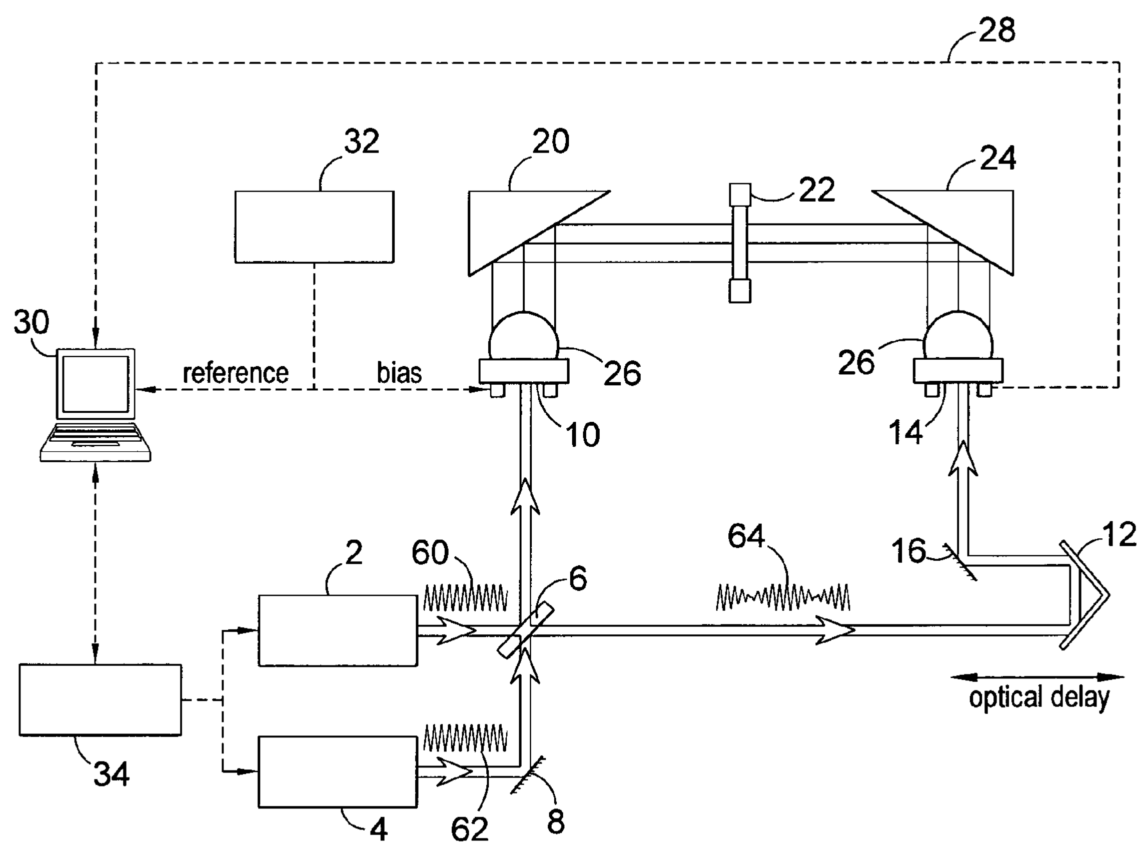
FIG. 1 is a schematic diagram of a terahertz spectrometer apparatus.

A terahertz spectrometer apparatus in the preferred embodiment is shown schematically in FIG. 1.

The spectrometer apparatus includes a first radiation source, in the form of a first DFB laser 2, and a second radiation source, in the form of a second DFB laser 4. Each of the DFB lasers has an output power of around 150 mW and a narrow single frequency linewidth of less than 4 MHz, and each may be temperature-tuned over a wide spectral range (over 1100 GHz) without mode-hop.

The first DFB laser 2 is directed at a beamsplitter 6. The second DFB laser 4 is directed at a mirror 8 which is arranged so that radiation from the second DFB laser is reflected towards the beamsplitter 6.

The beamsplitter 6 is arranged so that radiation arriving at the beamsplitter 6 from the first DFB laser 2 mixes with radiation arriving at the beamsplitter 6 from the second DFB laser 4, and so that the mixture of radiation is directed towards an emitter 10 and is also directed towards an optical delay device 12.

The optical delay device 12 is arranged so that radiation arriving from the beamsplitter 6 is directed to a detector 14 via a mirror 16.

Figure 2:
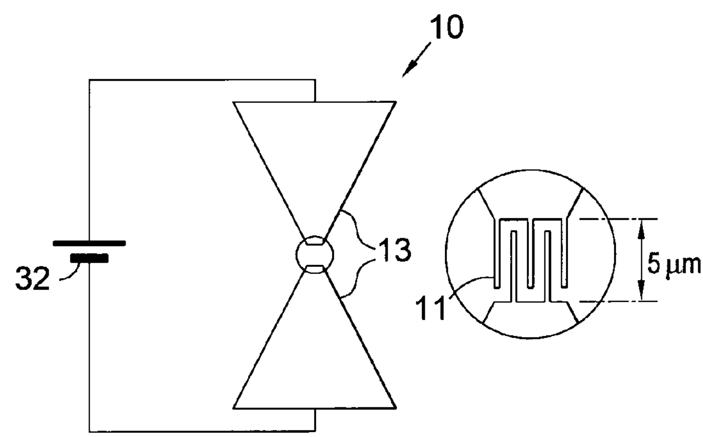
FIG. 2 is a schematic diagram of an emitter included in the apparatus of FIG. 1.

As shown schematically in FIG. 2, the emitter 10 comprises a photoconductive switch formed of interdigitated gold electrodes 11 connected via gold conductive regions 13 formed so as to operate as an antenna to a signal generator 32 for applying a bias voltage to the photoconductive switch.

A silicon lens 18 is positioned next to the emitter 10 and is arranged so that an output signal comprising electromagnetic radiation generated at the antenna of the emitter 10 passes through the silicon lens 18 and is directed to a mirror 20. The mirror 20 is arranged so that the electromagnetic radiation is then directed to a transmission cell 22.

In operation the transmission cell 22 usually contains a sample under investigation and is located in a sample space of the apparatus.

A further mirror 24 is located on the other side of the sample space from the mirror 20. The further mirror 24 is arranged so that electromagnetic radiation arriving at the further mirror 24 from the sample space is directed to a further silicon lens 26 positioned next to the detector 14.

The detector 14 comprises a further photoconductive switch (not shown) connected to an electrode (not shown) arranged to function as an antenna.

The further silicon lens 26 is arranged so that electromagnetic radiation arriving from the further mirror 24 is directed to the electrode of the detector 14.

As discussed in more detail later, in operation the detector 14 generates detection signals from the electromagnetic radiation received at the electrode of the detector 14.

The detector 14 is connected to control computer 30 by a connection 28, and in operation detection signals generated by the detector 14 are passed to the control computer 30 for processing and analysis. The control computer is programmed to control operation of the apparatus and to process and analyse detection signals.

The control computer 30 is also connected to the signal generator 32. The signal generator 32 is connected to the emitter 10 and, in operation, applies the bias voltage to the photoconductive switch of the emitter 10. The signal generator also provides a reference signal to the control computer 30, representative of, or identical to, the bias voltage.

The control computer 30 is connected to a temperature control unit 34 which is operable to control the respective temperature of each of the first DFB laser 2 and the second DFB laser 4.

The first DFB laser 2 and the second DFB laser 4 are both temperature tunable lasers and so, by controlling the temperature of each laser 2 4 the control computer 30, via the temperature control unit 34, is able to control the frequency of the radiation emitted by each laser 2 4.

The control of temperature of the DFB lasers 2 4 and the consequent control of frequency of the radiation emitted by the DFB lasers is now described with reference to FIG. 3.

The temperature control unit 34 comprises an analogue data acquisition card 36 and a thermal control unit 38. The thermal control unit is connected to a first Peltier heater/cooler 40 associated with the first DFB laser 2 and to a second Peltier heater/cooler 42 associated with the second DFB laser 4.

The first DFB laser 2 is located on a first base plate (not shown) to which the first Peltier heater/cooler 40 is thermally linked. The second DFB laser 4 is located on a second base plate (not shown) to which the second Peltier heater/cooler 42 is thermally linked. Thermometers (not shown) are attached to the first base plate and the second plate and are connected to the control computer 30 via the temperature control unit 34. In the preferred embodiment the thermometers are electrical resistance thermometers.

The control computer controls the temperature of each of the base plates using the Peltier heater/coolers 40 42, and so controls the temperature of the lasing cavities of the DFB lasers 2 4, which in turn determines the frequency of radiation emitted by each DFB laser 2 4.

In variants of the preferred embodiment, cooling water circuits 43 are also provided in order to cool the base plates.

Each of the DFB lasers 2 4 comprises a diode 44 46 and a collimator 48 50.

The collimator 48 of the first DFB laser 2 is arranged so that laser radiation generated by the first DFB laser 2 is directed to a beamsplitter 52. The beamsplitter 52 splits the laser radiation and directs some of the laser radiation to the beamsplitter 6 and some of the laser radiation to an optical spectrum analyser 54.

Similarly, the collimator 50 of the second DFB laser 4 is arranged so that laser radiation generated by the second DFB laser 4 is directed to a beam splitter 56. The beamsplitter 56 splits the laser radiation and directs some of the laser radiation to the beamsplitter 6 (via the mirror 8) and some of the laser radiation to a further optical spectrum analyser 58.

Each of the optical spectrum analysers 54 58 has a resolution of around 0.1 nm. Both optical spectrum analysers 54 58 are connected to the control computer 30.

Data from the optical spectrum analysers 54 58 and from the thermometers is used by the control computer 30 in a calibration procedure in which the frequency of the radiation emitted by each DFB laser 2 4 is correlated with the temperature of the respective base plate. The control computer 30 stores calibration data obtained from the calibration procedure, which it subsequently uses in order to determine, for each DFB laser, the temperature at which the DFB laser should be controlled in order to obtain radiation from the laser of any particular desired frequency.

Figure 3:
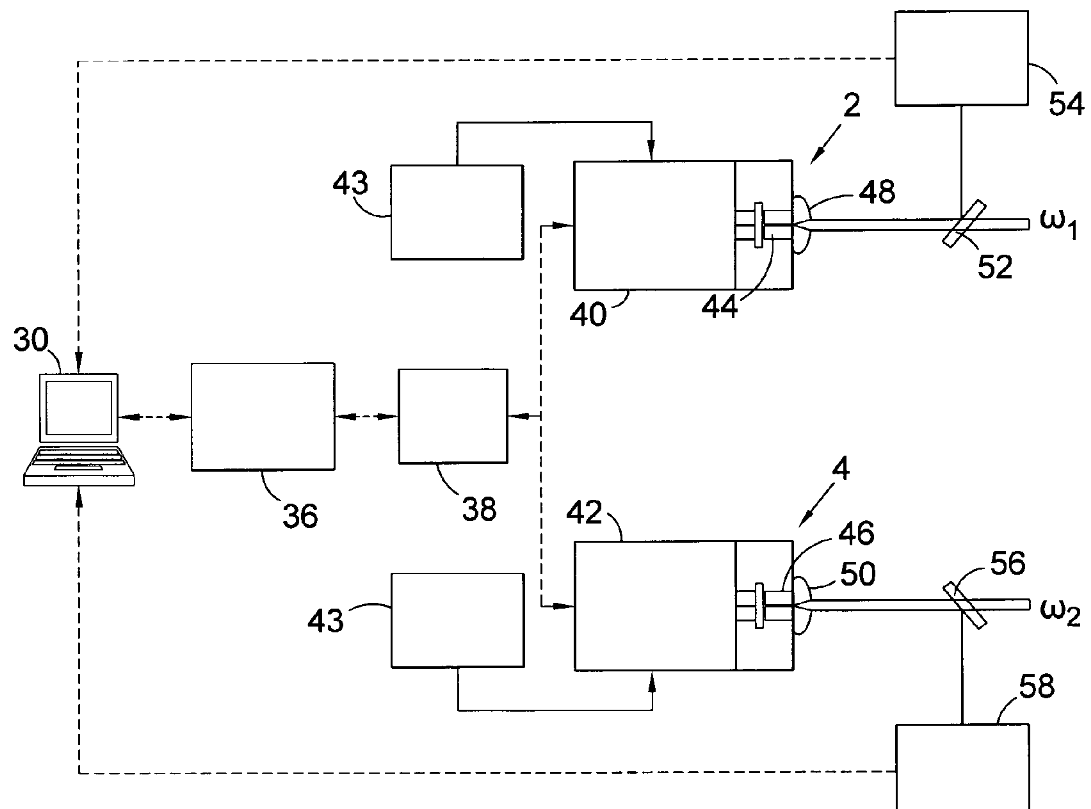
FIG. 3 is a schematic diagram of parts of the control circuitry for the DFB lasers of the apparatus of FIG. 1.

Operation of the spectrometer apparatus is now considered in more detail with reference to FIGS. 1, 2 and 3, and beginning with operation of the emitter 10 and the detector 14.

Operation of Emitter

As mentioned above, the emitter 10 comprises a photoconductive switch to which a bias voltage is applied by the signal generator 32. In the preferred embodiment the bias voltage is modulated at a kilohertz frequency, for instance 33 KHz. In variants of the preferred embodiment the bias voltage is a d.c. voltage.

Unless the photoconductive switch is illuminated with radiation of an appropriate frequency (typically infra-red or near infra-red radiation) it is in a highly resistive state and the bias voltage causes little or no current to flow through the photoconductive switch. When the photoconductive switch is illuminated with radiation of the appropriate frequency charge carriers are excited into the conduction band of the photoconductive switch and the bias voltage causes current to flow through the photoconductive switch. The number of charge carriers excited into the conduction band, and thus the conductivity of the photoconductive switch, is dependent on the amplitude of the radiation of the appropriate frequency.

The radiation emitted by the first DFB laser 2 and by the second DFB laser 4 is infra-red radiation or near infra-red radiation and is of a suitable wavelength such that when it is applied to the photoconductive switch of the emitter 10, charge carriers are excited and current flows through the photoconductive switch when a bias voltage is applied. Typically the preferred embodiment is arranged so that the first DFB laser 2 is tuned in wavelength between 779.53 nm and 782.27 nm, and so that the second DFB laser 4 is tuned in wavelength between 782.39 m and 785.09 nm.

In operation of the spectrometer apparatus, a mixture of radiation from the first DFB laser 2 and the second DFB laser 4 is applied to the photoconductive switch of the emitter 10 as mentioned above.

If the frequency of the radiation from the first DFB laser 2 is different to the frequency of the radiation from the second DFB laser 4 then the mixture of radiation applied to the photoconductive switch will have a characteristic beat frequency. Radiation 60 62 from the first DFB laser 2 and from the second DFB laser 4, and the resulting mixture of radiation 64 having a beat frequency is represented graphically in FIG. 1.

As the mixture of radiation applied to the photoconductive switch of the emitter 10 has a beat frequency, the conductivity of the photoconductive switch is modulated at the beat frequency, and in turn the current caused to flow through the photoconductive switch is modulated at the beat frequency.

As mentioned above, the photoconductive switch of the emitter 10 is connected to an electrode arranged to function as an antenna. In operation, current flowing through the photoconductive switch modulated at the beat frequency also flows through the electrode and causes the generation of electromagnetic radiation having a frequency of the modulating beat frequency.

In operation of the preferred embodiment, the difference between the frequency of radiation of the first DFB laser 2 and the second DFB laser is selected to be a desired value in the range 0.2 THz to 2 THz, with the electromagnetic radiation emitted by the emitter 10 thus having a frequency of that desired value.

Operation of Detector

As mentioned above the electromagnetic radiation generated at the emitter 10 is directed to the sample space via the silicon lens 18 and the mirror 20. The electromagnetic radiation passes through the sample space and to an electrode of the detector 14, via the further mirror 24 and the further silicon lens 26.

The detector 14 also comprises a photoconductive switch, which is connected to the electrode of the detector 14. The electrode is arranged to function as an antenna and electromagnetic radiation received at the electrode induces a voltage at the electrode.

As mentioned above, the electrode of the detector 14 is connected to a further photoconductive switch which is in turn connected to output circuitry of the detector 14. The voltage induced at the electrode of the detector 14 by receipt of the electromagnetic radiation causes current to flow to the output circuitry, with the magnitude of the current for a given induced voltage at a particular moment being dependent on the conductivity of the photoconductive switch at that moment.

As discussed above, the apparatus is arranged so that the photoconductive switch of the detector 14 also receives the mixture of radiation from the first DFB laser 2 and the second DFB laser 4. The conductivity of the photoconductive switch of the detector, and thus the sensitivity of detection of the detector, is modulated at the beat frequency of the mixture of radiation.

The detector 14 provides frequency-sensitive and phase-sensitive detection of electromagnetic radiation received at the electrode of the detector.

The optical delay device 12 is located between the beamsplitter 6 (where the radiation from the first DFB laser 2 and the second DFB laser 4 is mixed) and the detector 14. In the preferred embodiment the optical delay device is connected to the control computer 30 and the delay time between the mixture of radiation leaving the beamsplitter 6 and arriving at the detector 14 can be set, and varied, using the control computer 30. In alternative embodiments the optical delay device is adjusted, and the delay time set or varied, manually.

By varying the delay time, the relative phase of the electromagnetic radiation generated by the emitter 10 and the variation of conductivity of the photoconductive switch of the detector 14 (which corresponds to the sensitivity of detection of the detector 14) is varied.

In a preferred mode of operation, the delay time is dithered at a selected frequency by the optical delay device under the control of the control computer. Typically the selected dithering frequency is around 15 Hz. By dithering the delay time it is ensured that electromagnetic radiation at the modulating frequency (the beat frequency) received at the receiver is detected for all phases.

Spectroscopic Measurement

In the preferred mode of operation of the preferred embodiment, the mixture of radiation from the first DFB laser and the second DFB laser is applied continuously to the emitter (and to the receiver) over a relatively long period of time (for instance the reciprocal of the dither frequency, 67 ms in one mode of operation) whilst the temperature of each of the lasers is maintained at a particular desired value, before the temperature of one or other of the two lasers is varied to be another desired value. Thus the electromagnetic radiation generated by the emitter during the time that the temperature of each of the lasers is maintained at each particular desired value has a narrow range of frequencies, centred around the beat frequency. The mixture of radiation from the first DFB laser and the second DFB laser is continuous wave (CW) radiation.

As the electromagnetic radiation emitted by the emitter has a narrow range of frequencies, in order to obtain spectroscopic information concerning the sample across a desired range of frequencies, electromagnetic radiation at a succession of different frequencies within the desired range of frequencies is applied by the emitter 10 to the sample (by varying the temperature of the first DFB laser and/or the second DFB laser to have a succession of desired values). For the electromagnetic radiation at each of the succession of different frequencies, a response signal from the sample is received at the detector 14, and a corresponding output signal from the detector 14 is obtained.

Figure 4:
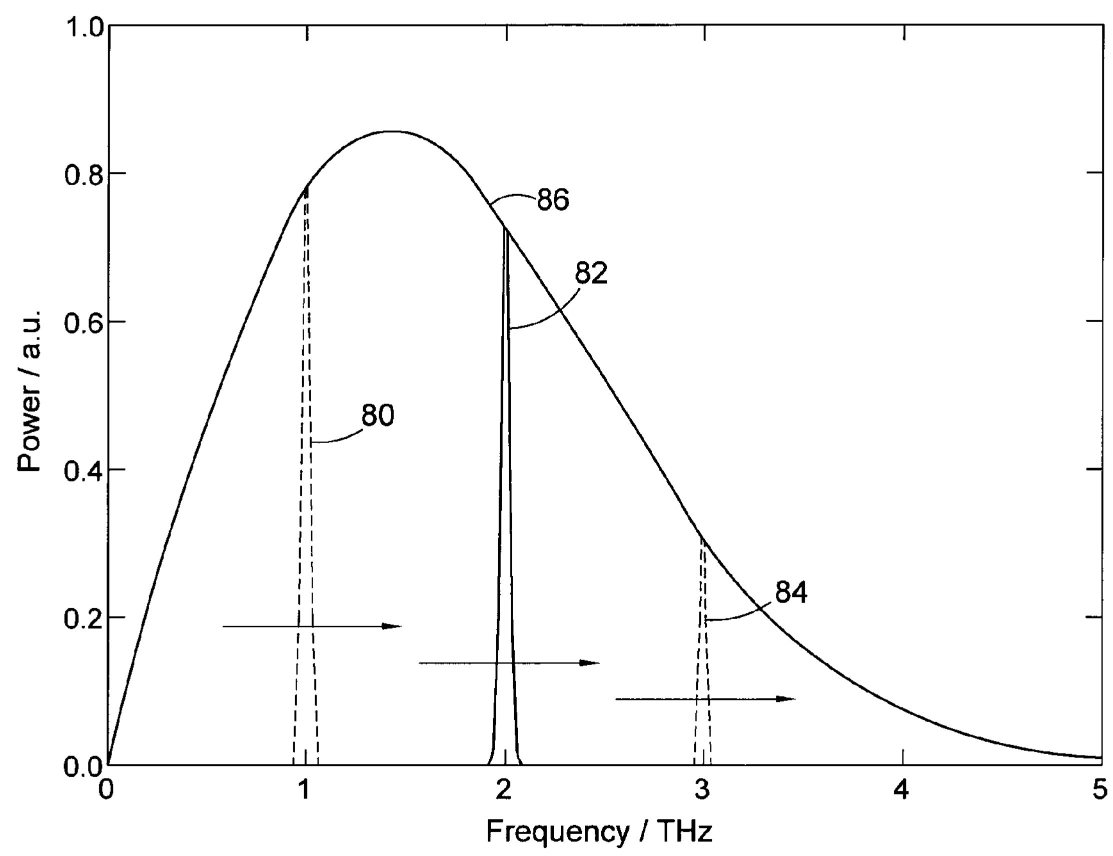
FIG. 4 is a graph showing the power and frequency characteristics of the electromagnetic radiation of continuous wave output signals produced by the emitter of the apparatus of FIG. 1, in comparison with power and frequency characteristics of a broadband pulse.

FIG. 4 shows the power (in arbitrary units) spectra 80 82 84 of electromagnetic radiation applied at three frequencies in a spectroscopic measurement according to the preferred embodiment. Each of the three spectra represents the electromagnetic radiation emitted by the emitter 10 when a mixture of radiation with a beat frequency of 1 THz, 2 THz and 3 THz respectively is applied to the photoconductive switch of the emitter 10. FIG. 4 is schematic and not to scale.

By way, of comparison the power spectrum of electromagnetic radiation emitted by the emitter 10 when a pulse of laser radiation is applied to the photoconductive switch of the emitter 10 is shown as solid line 82 (as an aside, it is noted that the power spectra shown in FIG. 4 for the pulsed and CW radiation are normalised to the radiation impedance of the antenna, representing the efficiency with which the antenna can couple different THz frequencies out of the emitter circuitry and into the silicon lens). It can be seen that the power spectrum has significant power at a very wide range of frequencies. If electromagnetic radiation with such a power spectrum is applied to a sample, the response signal from the sample contains components across all of a range of frequencies.

In contrast, in the preferred mode of operation, the electromagnetic radiation of the output signal of the emitter has a narrow range of frequencies and can be treated as if it is of a single frequency. The corresponding response signal, and the detection signal derived from the response signal, can then be treated as representing the response of the sample to electromagnetic radiation of a single frequency.

Accordingly, the control computer can process each detection signal, corresponding to a particular frequency, separately from other detection signals, corresponding to other frequencies, and can build up a frequency spectrum for a sample under consideration.

In the simplest case, the control computer plots, or otherwise outputs, the amplitude of each detection signal against the corresponding frequency.

In a case where the delay time is dithered at a particular frequency, each detection signal will vary with time as a function of the dither frequency. In that case, the control computer is programmed to fit each detection signal to a sinusoid varying with the dither frequency in order to extract the amplitude of that detection signal.

The control computer is programmed to compare each detection signal to a corresponding reference if so desired. The reference usually represents a calibration measurement taken using the apparatus in the absence of sample, and the control computer can be programmed to subtract an appropriate reference from each detection signal.

The control computer is also programmed to carry out a variety of signal processing techniques on the detection signals, if desired. Such signal processing techniques include signal averaging, signal summing, data fitting, data smoothing, selection of portions of data, and statistical analysis.

It can be understood from FIG. 4 that each successive measurement using the CW technique can provide frequency/amplitude information that is a subset of frequency/amplitude information that can be obtained from a single measurement using the pulsed technique (although in practice many measurements using the pulsed technique would typically be taken and signal averaged in order to obtain a reasonable signal to noise ratio across a desired frequency range).

A variant of the preferred mode of operation of the apparatus is now considered in more detail, and the mechanism for the acquisition of the terahertz spectrum is as follows.

The distribution of required frequency points in the spectrum is defined by three parameters: the beginning and end frequencies, and the frequency interval (resolution).

Front-end software running on the control computer 30 calculates from the beginning frequency the two required initial optical frequencies of the two lasers, and converts this to a pair of temperature values for the lasers according to a pre-determined calibration.

The temperature values are then used to calculate output voltages for the data acquisition card 36. The temperature tuning sensitivity in the preferred embodiment is approximately 27 GHz/K, with a safe operational tuning range of approximately 40 K (5° C. to 45° C.). Thus if both DFB lasers are tuned, and have appropriate centre frequencies, a difference frequency range of 0-2.2 THz is permitted.

The analogue computer interface allows for a temperature control to within 1 mK or better, corresponding to an instrument resolution of at least 30 MHz in the preferred embodiment.

The spectral power is derived from the photoconductive detector 14 by dithering a time delay stage 12 at 15 Hz and recording the waveform at each point.

Since the frequency is already known to a far greater precision than can be measured from the collected data, only the amplitude and phase are recorded. The two parameters, amplitude and phase, are obtained from the output signal by using a sinusoidal curve fit of the output signal as a function of the position of the time delay sweep in the 15 Hz cycle, thus allowing the signal as a function of time to be reconstructed. Thus the amplitude may therefore be directly recorded from the time domain. No Fourier transform of the output signal is necessary in order to obtain the value of the amplitude.

Figure 5:
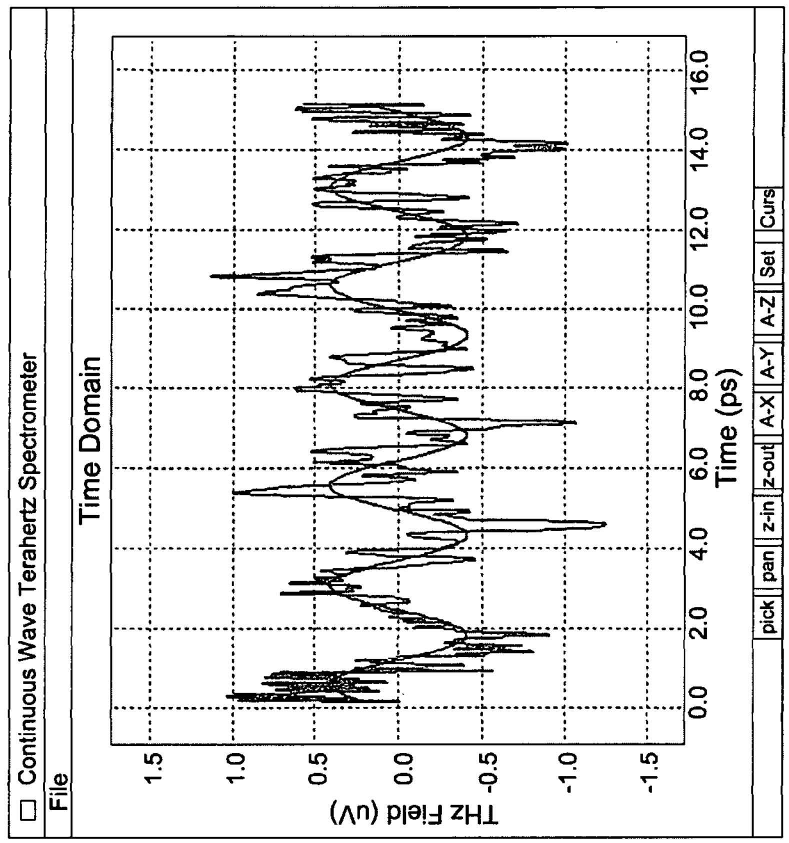
FIG. 5 is a pair of graphs showing examples of two sinusoidal fits of output signal as a function of the position of the time delay sweep (one for a relatively strong signal and one for a relatively weak signal)
Figure 5:
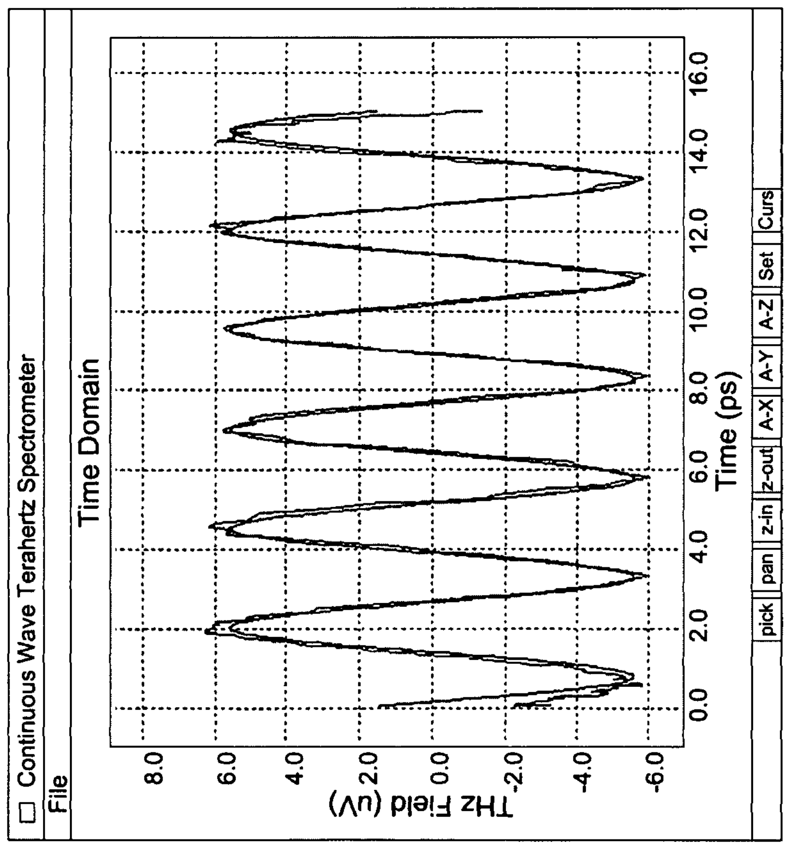

An example of two sinusoidal fits of output signal as a function of the position of the time delay sweep (one for a relatively strong signal and one for a relatively weak signal) are shown in FIG. 5.

The amplitude (related to the power) may be used to define the spectrum, given a suitable reference, and is therefore typically plotted against the current tuned terahertz frequency.

The software then calculates the temperature corresponding to the next required frequency value, and moves the laser frequencies to their new values. The acquisition time for each point in the frequency domain may be varied according to the required signal-to-noise ratio, but in practice is limited to a minimum value of 67 ms for a 15 Hz delay dither. Thus, in this configuration, signal-to-noise permitting, a modest 1000 point spectrum may be collected in just over one minute.

Figure 6:
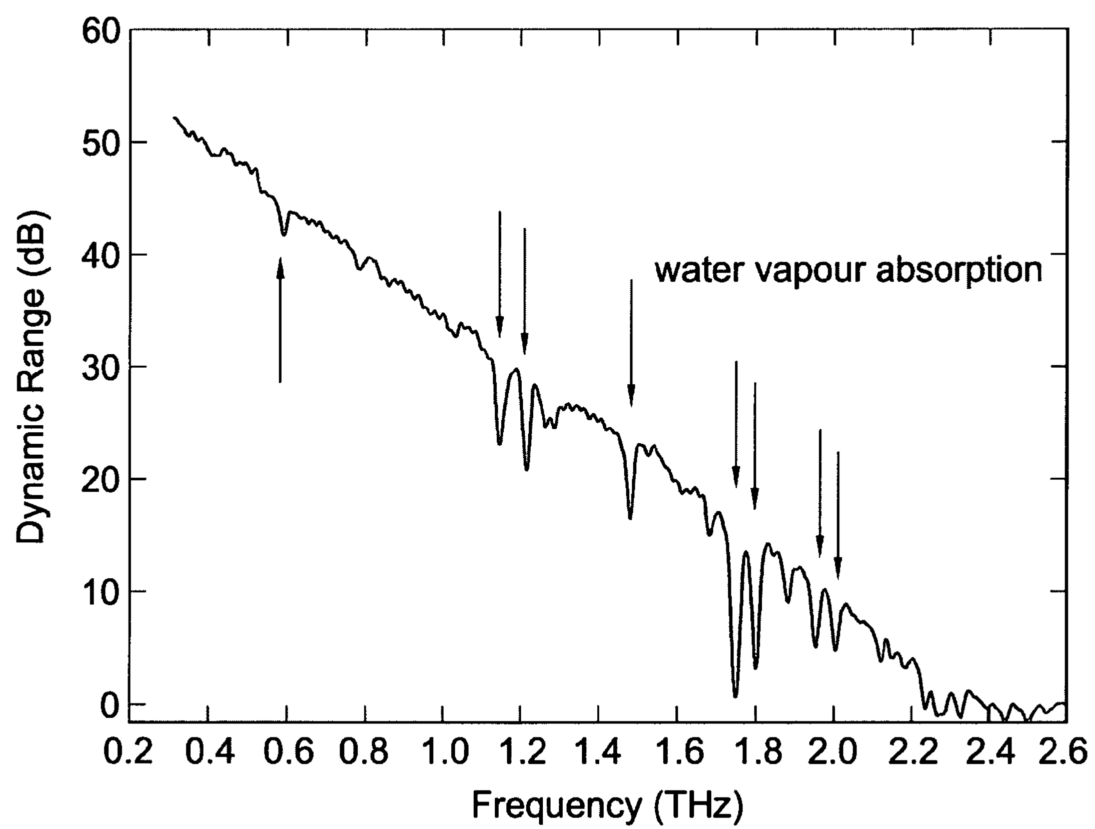
FIG. 6 is an example of a terahertz absorption spectra for a sample of water vapour.
Figure 7:
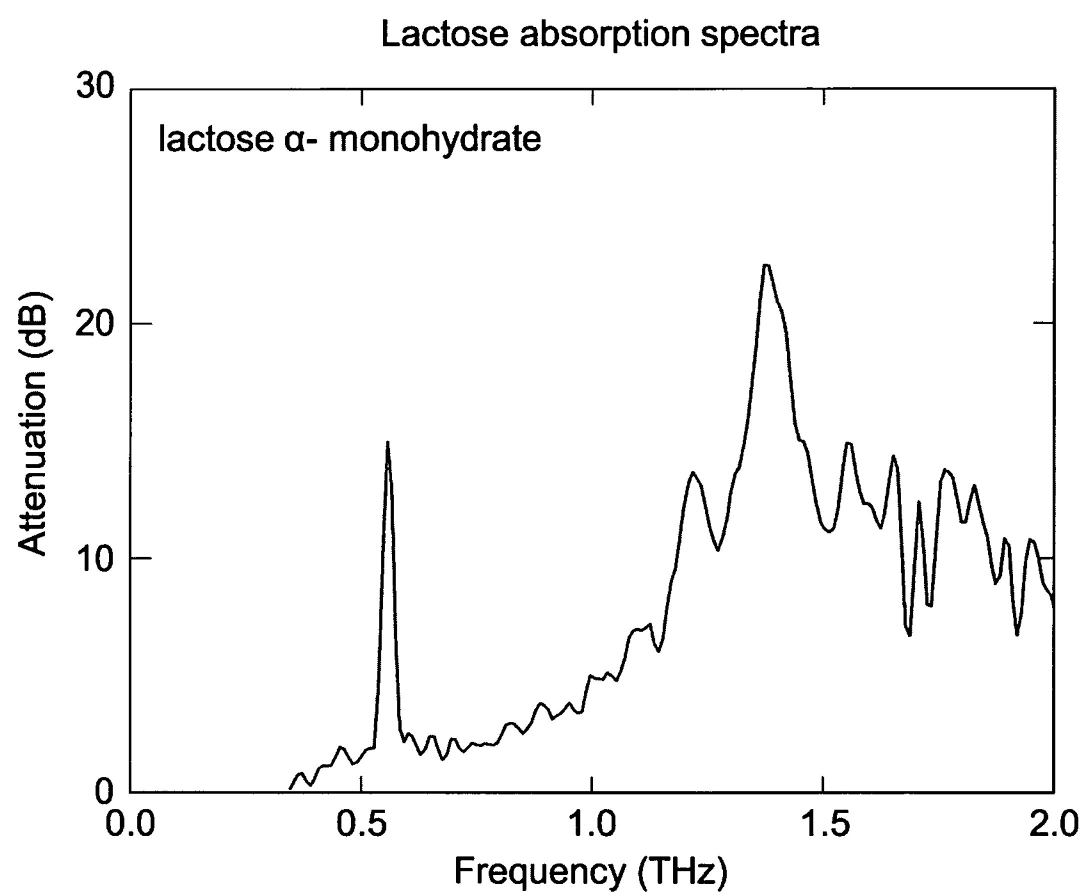
FIG. 7 is an example of a terahertz absorption spectra for a sample of lactose a-monohydrate.

Two examples of terahertz absorption spectra, for water vapour and lactose a-monohydrate respectively, are shown in FIGS. 6 and 7. Relative amplitudes of the response signal, on a dB scale, are plotted against frequency in THz.

Avoidance of Mode Hop

It is important, particularly for spectroscopic measurements, that the frequency of electromagnetic radiation of an output signal applied to a sample can be varied over a range of frequency of interest without causing mode hops in a lasers or lasers used to generate the electromagnetic radiation. Such mode hops result in large jumps in frequency of the electromagnetic radiation and make it difficult or impossible to take measurements at a succession of increasing or decreasing frequencies.

In the preferred embodiment, the DFB lasers are selected to have sufficiently wide mode-hop free tuning ranges to enable electromagnetic radiation to be generated having any frequency in a range of frequency of interest.

In variants of the preferred embodiment the control computer 30 is programmed to ensure that in controlling the temperature of the two DFB lasers to obtain a desired frequency difference between the two lasers, and thus to enable generation of electromagnetic radiation of a desired frequency, no mode-hop occurs in either of the two DFB lasers.

In certain variants, a range of temperature for the first DFB laser and a range of temperature for the second DFB laser is pre-determined, each range of temperature being a range of temperature over which no mode-hop occurs for the respective laser. Typically, the control computer is programmed to store, for instance as a look-up table or an algorithm, and/or to use such pre-determined ranges of temperature in determining temperatures of the DFB lasers to be used to generate electromagnetic radiation of a desired frequency.

In certain variants, the first pre-determined range of temperature and the second pre-determined range of temperature are different, and are arranged so that they just overlap. In such a way the range of frequency of the generated electromagnetic radiation which can be obtained without mode hop, by varying the temperatures within the pre-determined ranges of temperature, is maximised.

Reflection Geometry

In the preferred embodiment described above, the detector and emitter are arranged in a transmission geometry. In alternative embodiments, the detector and emitter are arranged in a reflection geometry rather than in a transmission geometry. In such an arrangement, the emitter is positioned so as to transmit electromagnetic radiation towards a sample space, or target region, and the detector is positioned so as to receive electromagnetic radiation reflected from the sample space, or target region. In contrast, in a transmission geometry such as that illustrated in FIGS. 1, 2 and 3, the emitter and detector are positioned so that the detector receives radiation transmitted by the emitter through a sample space.

Figure 8:
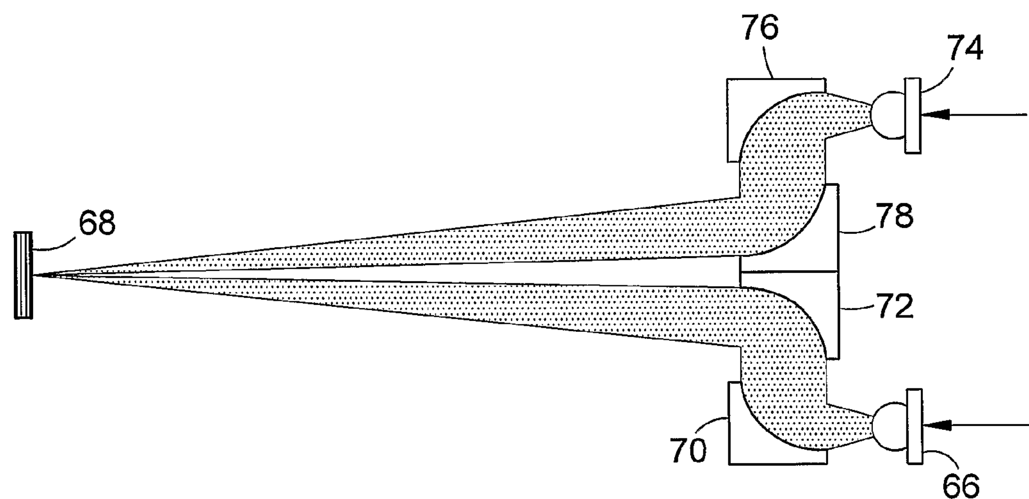
FIG. 8 is a schematic diagram showing the arrangement of an emitter and a detector in a terahertz detection apparatus in an alternative embodiment.

An example of an alternative embodiment in which the detector and emitter are arranged in a reflection geometry is shown schematically in FIG. 8.

An emitter 66 is arranged so as to transmit electromagnetic radiation towards a target 68 in a target region via an arrangement of mirrors 70 72. The mirrors 70 72 are arranged so as to focus the electromagnetic radiation onto the target region.

A detector 74 is arranged so as to receive electromagnetic radiation from the target region via a further arrangement of mirrors 76 78. The mirrors 76 78 are arranged so as to focus electromagnetic radiation from the target region onto the detector 74.

It can be seen from FIG. 8 that the emitter 66 and the detector 74 face in substantially the same direction and that in operation, when a target is present in the target region, electromagnetic radiation received by the detector 74 comprises electromagnetic radiation transmitted by the emitter 66 and then reflected, backscattered, or absorbed and re-emitted, by the target 68.

The emitter 66 is substantially the same as the emitter 10 described in relation to FIGS. 1, 2 and 3. Similarly the detector 74 is substantially the same as the detector 14 described in relation to FIGS. 1, 2 and 3. Also, with the exception of the mirrors 20 24 and the transmission cell 22 the alternative embodiment illustrated in FIG. 8 further comprises the components of the preferred embodiment described in relation to FIGS. 1, 2 and 3.

Further Applications

The apparatus of the preferred embodiment may be used for carrying out spectroscopic measurements on a sample which is known to be present, in order to obtain information concerning the physical and electronic structure of the sample, as described above.

In alternative modes of operation of the preferred embodiment and in alternative embodiments, the presence or absence of a substance of interest which is not known to be present, and which may be concealed within a sample, another substance or a target is detected.

Figure 9:
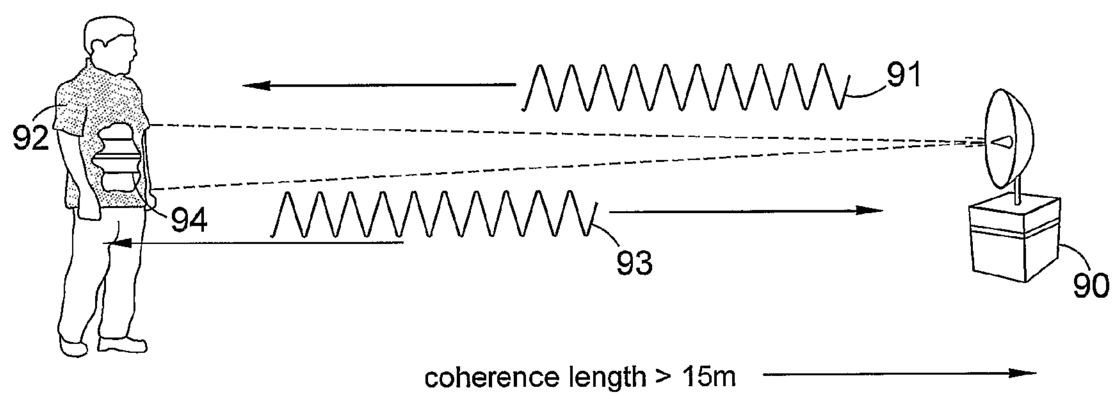
FIG. 9 is a schematic diagram of a terahertz detection apparatus for detection of a concealed substance in an alternative embodiment.

An example of an alternative embodiment is shown schematically in FIG. 9. A detection apparatus 90 is arranged to transmit an output signal 91 comprising electromagnetic radiation towards a person 92 located in a target region or sample space, and to receive a response signal 93. The response signal includes electromagnetic radiation reflected from a substance of interest 94 concealed about the person 92.

The detection apparatus 90 has the same components as the apparatus illustrated in FIG. 8.

In one mode of operation, a full frequency spectrum, is measured as described above in relation to the preferred embodiment and then the frequency spectrum is compared to the expected frequency spectrum of the substance of interest to determine whether the substance of interest is present.

In another alternative mode of operation for detecting the presence or absence of a substance, instead of measuring a full frequency spectrum particular characteristics of the substance of interest are identified and terahertz electromagnetic radiation of suitable frequency is applied in order to determine whether a substance is present which possesses those particular characteristics. The presence or absence of the substance of interest is determined in dependence on whether the output signal from the detector in response to the electromagnetic radiation is consistent with the substance of interest being present.

For example, in one mode of operation, it is identified that the substance of interest absorbs radiation strongly at particular terahertz frequencies or, alternatively, reflects radiation strongly at particular terahertz frequencies. Electromagnetic radiation is then applied successively at one or more of those particular frequencies and the presence or absence of the substance of interest is determined in dependence on whether the output signal from the detector in response to the electromagnetic radiation is consistent with the substance of interest being present.

Similarly, in another mode of operation, it is identified that the substance of interest causes particular phase shifts to electromagnetic radiation applied at particular terahertz frequencies. Again, electromagnetic radiation is then applied successively at one or more of those particular frequencies and the presence or absence of the substance of interest is determined in dependence on whether the output signal from the detector in response to the electromagnetic radiation is consistent with the substance of interest being present.

As continuous wave (CW) output signals are used, the coherence length of the electromagnetic radiation of the output signals is relatively long.

The coherence length in the time domain is effectively the reciprocal of the linewidth in the frequency domain. If the phase is known at one position then it can be predicted for a distance equal to the coherence length. By way of example, a perfect single frequency sine wave has zero linewidth in the frequency domain and is infinitely coherent in the time domain. In contrast, in a practical example, a THz system using femtosecond pulses produces THz radiation with a broad frequency spectrum and a correspondingly short coherence length (typically a few hundred μm).

Thus generally pulsed THz systems are not useful for measurement of samples whose position is not well defined and which may be present somewhere over a range of distances.

In contrast it is a feature of certain alternative embodiments, such as those of FIGS. 8 and 9, that an output signal is provided which has a coherence length which is sufficiently large to enable the measurement or detection of a sample or substance of interest which is, or may be, present anywhere within a relatively large range of distance from the emitter. For instance in the embodiment of FIG. 9, an output signal is provided which has a coherence length of greater than 15 m. In variants of the embodiment, an output signal is provided which has a coherence length of greater than or equal to 5 m, greater than or equal to 10 m, or even greater than or equal to 20 m.

In variants of the embodiments described herein the control computer is adapted to generate an alarm signal. When such alternative embodiment is used to detect the presence or absence of a substance of interest which is not known to be present, the control computer is programmed to generate an alarm signal if an output signal, or output signals, from the detector is greater than a pre-determined threshold. The output signals may be processed, for instance by signal summing or averaging, or by combination of output signals of different frequencies or phases, before comparison with the threshold. Typically, such embodiments further comprise an audible or visual alarm, operable in response to the alarm signal.

The preferred embodiment described above provides a terahertz spectrometer which offers a superior spectral resolution to a broadband spectrometer, using compact and inexpensive diode lasers. The tunable mode-hop-free range is superior to that afforded by conventional DBR diode lasers, and no moving parts or external cavities are required in the laser head.

It will be understood that the invention has been described above purely by way of example, and modifications of detail can be made within the scope of the invention.

Each feature disclosed in the description and (where appropriate) the claims and drawings may be provided independently or in any appropriate combination.

The invention claimed is:

1. Apparatus for measurement of a sample, comprising:

means for generating electromagnetic radiation comprising a photoconductive device, the generating means being arranged to generate an output signal comprising electromagnetic radiation in dependence upon radiation received by the photoconductive device and to transmit the output signal towards a sample space;

a first radiation source and a second radiation source, arranged such that the radiation received by the photoconductive device comprises a mixture of radiation from the first radiation source and radiation from the second radiation source;

control means for varying the frequency of the electromagnetic radiation of the output signal by varying the temperature of the first radiation source and/or the temperature of the second radiation source; and detecting means for detecting a response signal, wherein the control means is adapted to vary the temperature of the first radiation source within a first pre-determined range of temperature and to vary the temperature of the second radiation source within a second pre-determined range of temperature, wherein each of the first pre-determined range of temperature and the second pre-determined range of temperature is a range of temperature within which no mode hop occurs in the first radiation source or in the second radiation source respectively.

2. Apparatus according to claim 1, wherein the electromagnetic radiation of the output signal comprises continuous wave (CW) radiation.

3. Apparatus according to claim 1, wherein the radiation from the first radiation source comprises continuous wave (CW) radiation and the radiation from the second radiation source comprises continuous wave (CW) radiation.

4. Apparatus according to claim 1, wherein the output signal comprises electromagnetic radiation having a frequency/power spectrum with a half-power width of less than 10 GHz.

5. Apparatus according to claim 1, wherein the generating means comprises an antenna arranged so that the value of the electrical current through the antenna is dependent on the conductivity of the photoconductive device, and preferably the conductivity of the photoconductive device is dependent on the mixture of radiation received by the photoconductive device.

6. Apparatus according to claim 1, arranged so that the frequency of the electromagnetic radiation of the output signal is dependent on the difference between the frequency of the radiation from the first radiation source and the frequency of the radiation from the second radiation source.

7. Apparatus according to claim 6, arranged so that the frequency of the electromagnetic radiation of the output signal is dependent on a beat frequency of the mixture of radiation from the first radiation source and radiation from the second radiation source received at the photoconductive device.

8. Apparatus according to claim 1, wherein the control means is adapted to vary the frequency of the electromagnetic radiation of the output signal so as to provide electromagnetic radiation successively at each of a plurality of frequencies in the selected range of frequencies.

9. Apparatus according to claim 1, wherein the control means is adapted to vary the frequency of the electromagnetic radiation of the output signal so as to scan the frequency of the electromagnetic radiation of the output signal across the selected range of frequencies or part of the selected range of frequencies.

10. Apparatus according to claim 1 wherein the selected range of frequencies is in the range 0 THz to 10 THz.

11. Apparatus according to claim 1, wherein the control means is adapted to vary the temperature of the first radiation source and/or the second radiation source in such a way as to ensure that no mode-hop occurs in the first radiation source or the second radiation source.

12. Apparatus according to claim 1, wherein the width of each of the first pre-determined range of temperature and the second pre-determined range of temperature is $\leqq$20K.

13. Apparatus according to claim 1, wherein the frequency of the radiation emitted by the first radiation source at the lowest extreme of the first pre-determined range of temperature is different from the frequency of the radiation emitted by the second radiation source at the lowest extreme of the second pre-determined range of temperature.

14. Apparatus according to claim 1, wherein the frequency of the radiation emitted by the first radiation source at the highest extreme of the first pre-determined range of temperature is substantially the same as the frequency of the radiation emitted by the second radiation source at the lowest extreme of the second pre-determined range of temperature.

15. Apparatus according to claim 1, wherein the control means is adapted to maintain the frequency of the radiation from the first radiation source substantially constant and the frequency from the second radiation source substantially constant for a pre-determined period of time.

16. Apparatus according to claim 1, wherein the detecting means comprises a further photoconductive device.

17. Apparatus according to claim 16, wherein the detecting means has a sensitivity of detection of the response signal which is modulated at a modulation frequency in dependence upon modulating radiation received by the further photoconductive device.

18. Apparatus according to claim 17, wherein the detecting means is arranged so that the modulating radiation received by the further photoconductive device comprises a mixture of radiation from at least two radiation sources, and the control means is adapted to vary the modulation frequency at which the sensitivity of detection is modulated by varying the temperature of at least one of the at least two radiation sources.

19. Apparatus according to claim 1, wherein the detecting means is adapted to generate a detection signal representative of the response signal, and the apparatus further comprises processing means for processing the detection signal.

20. Apparatus according to claim 19, wherein the processing means is adapted to fit the variation of the detection signal with time to a function.

21. Apparatus according to claim 19, wherein the processing means is adapted to compare the detection signal to a reference.

22. Apparatus according to claim 19, wherein the processing means is adapted to compare the detection signal to a pre-determined threshold, and preferably is adapted to generate an alarm signal in dependence on the comparison.

23. Apparatus according to claim 1, wherein at least one of, and preferably each of, the first radiation source, the second radiation source, the first radiation source for the detecting means and the second radiation source for the detecting means comprises a respective temperature-tunable laser.

24. Apparatus according to claim 23, wherein at least one of the temperature-tunable lasers comprises a respective distributed feedback (DFB) laser.

25. Apparatus according to claim 23, wherein each temperature-tunable laser is adapted to output near infra-red radiation or infra-red radiation.

26. Apparatus according to claim 23, wherein each temperature-tunable laser is adapted to output radiation with a centre wavelength in the range 760 nm to 1090 nm.

27. Apparatus according to claim 1, further comprising a sample cell adapted to be located in the sample space and to contain a sample.

28. Apparatus according to claim 1, wherein the means for generating electromagnetic radiation is arranged to generate electromagnetic radiation having a coherence length $\geqq 5$ m.

29. Apparatus according to claim 1, being a terahertz spectrometer.

30. Apparatus according to claim 1, wherein the width of each of the first pre-determined range of temperature and the second pre-determined range of temperature is $\leqq 40$K.

31. Apparatus according to claim 1, wherein the width of each of the first pre-determined range of temperature and the second pre-determined range of temperature is $\leqq 50$K.

32. Apparatus for measurement of a sample, comprising:

means for generating electromagnetic radiation, arranged to generate an output signal comprising electromagnetic radiation and to transmit the output signal towards a sample space;

detecting means for detecting a response signal, the detecting means comprising a photoconductive device and being arranged so that the sensitivity of detection of the response signal is modulated at a modulation frequency in dependence upon modulating radiation received by the photoconductive device;

a first radiation source for the detecting means and a second radiation source for the detecting means, arranged such that the modulating radiation received by the photoconductive device comprises a mixture of radiation from the first radiation source for the detecting means and radiation from the second radiation source for the detecting means;

control means for varying the modulation frequency at which the sensitivity of detection is modulated, the control means being adapted to vary the modulation frequency by varying the temperature of the first radiation source for the detecting means and/or the temperature of the second radiation source for the detecting means, wherein the control means is adapted to vary the temperature of the first radiation source within a first pre-determined range of temperature and to vary the temperature of the second radiation source within a second pre-determined range of temperature, wherein each of the first pre-determined range of temperature and the second pre-determined range of temperature is a range of temperature within which no mode hop occurs in the first radiation source or in the second radiation source respectively.

33. Apparatus according to claim 32, wherein the detecting means comprises an antenna arranged so that value of electrical current through the antenna is dependent on the conductivity of the photoconductive device, and preferably the conductivity of the photoconductive device is dependent on the mixture of radiation received by the photoconductive device.

34. Apparatus according to claim 32, further comprising guide means for guiding radiation from the first radiation source and the second radiation source to the photoconductive device of the generating means and to the photoconductive device of the detecting means.

35. Apparatus according to claim 34, wherein the guide means comprises delay means adapted to provide a delay between radiation from the first radiation source and the second radiation source being received at the photoconductive device of the generating means and being received at the photoconductive device of the detecting means.

36. Apparatus according to claim 35, wherein the control means is adapted to control the length of the delay to be a desired delay time.

37. Apparatus according to claim 35, wherein the control means is adapted to vary the delay time.

38. Apparatus according to claim 37, wherein the delay means is adapted to vary the delay time with a pre-determined frequency.

39. A method of measurement of a sample, comprising:

generating an output signal comprising electromagnetic radiation by applying a mixture of radiation from a first radiation source and radiation from a second radiation source to a photoconductive device, and transmitting the output signal towards a sample space;

varying the frequency of the electromagnetic radiation of the output signal by varying the temperature of the first radiation source and/or the temperature of the second radiation source; and detecting a response signal, wherein the temperature of the first radiation source is varied within a first pre-determined range of temperature and the temperature of the second radiation source is varied within a second pre-determined range of temperature, wherein each of the first pre-determined range of temperature and the second pre-determined range of temperature is a range of temperature within which no mode hop occurs in the first radiation source or in the second radiation source respectively.

40. A method of measurement of a sample, comprising:

providing means for generating an output signal comprising electromagnetic radiation and transmitting the output signal towards a sample space;

providing a detecting means for detecting a response signal;

modulating the sensitivity of detection of the detecting means at a modulating frequency by applying a mixture of radiation from a first radiation source and from a second radiation source to a photoconductive device included in the detecting means; and varying the frequency at which the sensitivity of detection is modulated by varying the temperature of the first radiation source and/or the temperature of the second radiation source, wherein the temperature of the first radiation source is varied within a first pre-determined range of temperature and the temperature of the second radiation source is varied within a second pre-determined range of temperature, wherein each of the first pre-determined range of temperature and the second pre-determined range of temperature is a range of temperature within which no mode hop occurs in the first radiation source or in the second radiation source respectively.

* * * * *